United States Patent [19]
Ito et al.

[11] Patent Number: 5,690,610
[45] Date of Patent: Nov. 25, 1997

[54] ADHESIVE MATERIAL FOR HEMOSTASIS AND A METHOD FOR HEMOSTASIS

[75] Inventors: Toshio Ito, Tokyo; Takayuki Akutsu; Tsugio Saito, both of Iruma; Takayoshi Numata, Kawagoe; Fumio Tokumura; Katsumi Kusumi, both of Iruma; Kunihiro Ohyama, Tsurugashima, all of Japan

[73] Assignee: Nichiban Co., Ltd., Japan

[21] Appl. No.: 209,537

[22] Filed: Mar. 10, 1994

[30] Foreign Application Priority Data

| Mar. 4, 1991 | [JP] | Japan | 6-060144 |
| Mar. 10, 1993 | [JP] | Japan | 5-075028 |
| May 20, 1993 | [JP] | Japan | 5-139833 |

[51] Int. Cl.[6] ............................................ A61F 13/00
[52] U.S. Cl. .................. 602/53; 602/46; 602/56; 604/305
[58] Field of Search ................. 602/42, 43, 53, 602/54, 58, 46, 56; 604/304, 305

[56] References Cited

U.S. PATENT DOCUMENTS

| 2,280,506 | 4/1942 | Betts | 602/53 |
| 3,490,448 | 1/1970 | Grubb | 601/53 |
| 3,908,645 | 9/1975 | Sandvig | 128/97 |
| 4,005,709 | 2/1977 | Laendal | 602/53 |
| 4,235,337 | 11/1980 | Dotta | 206/441 |
| 4,377,159 | 3/1983 | Hansen | 602/53 |
| 4,390,519 | 6/1983 | Sawyer | 424/28 |
| 4,418,822 | 12/1983 | Dotta | 206/441 |
| 4,561,435 | 12/1985 | McKnight et al. | 128/156 |
| 4,743,499 | 5/1988 | Volke | 428/317.3 |
| 4,803,078 | 2/1989 | Sakai | 424/445 |
| 4,907,579 | 3/1990 | Kum | 128/156 |
| 5,125,401 | 6/1992 | Gerhartl | 602/52 |

*Primary Examiner*—Mark Bockelman
*Assistant Examiner*—Chalin Smith
*Attorney, Agent, or Firm*—Adams & Wilks

[57] ABSTRACT

A sticking material for hemostasis has a flexible strip-shaped base member having a high recovery property, a main surface, and side edges extending in a first longitudinal direction. An adhesive layer is disposed on the main surface of the base member. A pad is disposed on the adhesive layer and extends in a second longitudinal direction substantially transverse to the first longitudinal direction such that a space is defined between the pad and each of the side edges of the base member. The pad is of a size sufficient to exert pressure at a puncture area including punctures of both a blood vessel and a skin surface. The pad has a slight elasticity and a hardness capable of securely exerting pressure on the punctures by a shrinking action of the base member when the base member is adhered to the skin surface while being stretched to secure the pad over the punctures. A pressure plate having a width equal to or less than the width of the base member may be interposed between the base member and the pad to enable the pad to be more strongly pressed against the puncture area. The pressure plate has a size greater than the size of the pad. Hemostasis is conducted readily and effectively without the possibility of blood leaking from the puncture area.

24 Claims, 8 Drawing Sheets

ADHESIVE MATERIAL FOR HEMOSTASIS AND A METHOD FOR HEMOSTASIS

BACKGROUND OF THE INVENTION

(1) Field of the Invention

The present invention relates to an adhesive or sticking material for hemostasis, i.e., a hemostatic adhesive bandage, and a method for hemostasis.

(2) Background Information

In recent years, therapies and tests involving arterio puncture, such as arterio puncture catheter, arteriography or inter arterial injection, have been widely conducted. The arterio puncture catheter is widely conducted for the purpose of monitoring the blood pressure of an artery during an operation and collecting the blood from the artery to check the conditions of the lungs based on the blood condition. The arterio puncture catheter is also applied to hemodialysis or the like. Arteriography is widely used not only for diagnosis, but also for the procedures of arterial embolism and percutaneous transcatheter angioplasty.

Heretofore, when therapies and tests involving arterio puncture are conducted, in many cases, after the therapy or the like, the injection needle, catheter, therapeutic tube or the like is removed from the ductus arteriosus, and finger pressure is applied to the area from which it is removed (the puncture area) for at least about 10 minutes. Then, a gauze is placed over the puncture area and a large pillow-like pad is put thereon and then fastened to apply pressure to the ductus arteriosus for hemostasis. After hemostasis is achieved, the patient is returned to a ward or the like. After such therapies involving arterio puncture, the hemostasis treatments are made by doctors or nurses. However, the doctors or nurses have much work to do after the therapy, and it is therefore desired to improve the hemostasis procedure.

For the hemostasis of an artery, there is no adequate procedure at present which performs it readily and effectively due to the high blood pressure of about 100 to 150 mmHg.

SUMMARY OF THE INVENTION

It is an object of the present invention to make it possible to conduct hemostasis readily and securely during therapies or tests involving the puncture of the ductus arteriosus by an injection needle or the like and then the removal of the injection needle or the like at the puncture area of the artery.

According to the present invention, at one surface of a base material made of a stretchable material having a recovery property, an adhesive layer is disposed. On the adhesive layer, is placed a pad with an adequate thickness, having a hardness while having a slight elasticity, one size of which is able to press both the puncture of the arterial blood vessel and the puncture of the skin surface at the same time. The sticking material is stuck to the puncture area, and the puncture of the arterial blood vessel is pressed tightly for hemostasis with the pad, while absorbing the bleeding blood from the puncture of the skin surface with the pad, to thereby securely conduct the hemostasis.

Further, according to the present invention, the pad is placed to cover the puncture area of the arterial blood vessel, and a pressing plate larger in size than the pad is placed on the pad. The pressing plate and pad are fixed to the wound area in the vicinity of the puncture area with a base material having an adhesive, whereby the pressing action of the pad is strengthened by the pressing plate and the puncture area of the arterial blood vessel is pressed, to thereby securely conduct hemostasis.

Furthermore, according to the present invention, a pad is placed to cover the puncture area of the arterial blood vessel, a pressing plate larger in size than the pad is placed on the skin surface at the side opposite to the skin surface on which the pad is placed with the arterial blood vessel interposed, and then the pad and the pressing plate are fixed with a base material having an adhesive to surround the arterial blood vessel of the wound area, whereby the pad is pressed against the puncture area for hemostasis.

The above and other objects and features of the present invention will become apparent to persons of ordinary skill in the art by reference to the following description when read in connection with the accompanying drawings.

DETAILED DESCRIPTION OF THE INVENTION

Figure 1:
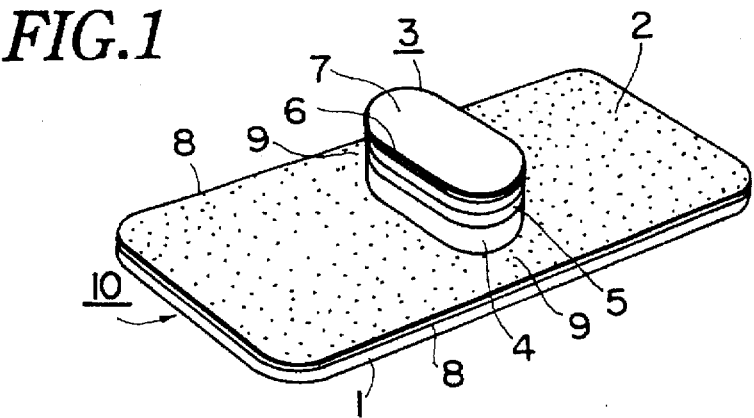
FIG. 1 is a perspective view showing an embodiment of the sticking material for hemostasis according to the present invention.

The present invention will be described hereinafter with reference to the various embodiments thereof shown in the drawings.

Figure 2:
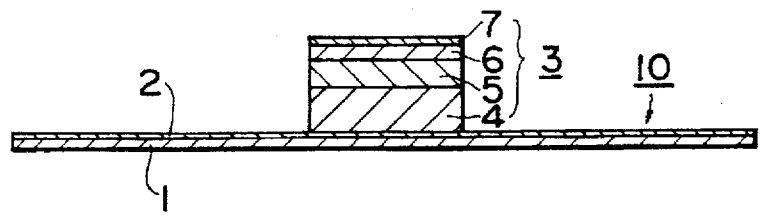
FIG. 2 is a cross-sectional view of the sticking material shown in FIG. 1.

In FIGS. 1 and 2, an adhesive or sticking material 10 for hemostasis comprises an adhesive layer 2 is formed on one surface of a substrate or base material 1. For the base material 1, various materials such as a plastic sheet, woven cloth and unwoven cloth, may be employed. If materials having stretchability are employed, when the base material is adhesively stuck over the puncture area while being stretched, the material tends to shrink after sticking, whereby the pad will be more effectively pressed to the puncture area.

When the sticking material is used for hemostasis of an artery, the base material 1 is preferably made of a stretchable material having a high recovery property, and base materials having a 100% extensibility (a stress exerted when it is extended to 100%) of about 4.4 to 5.9 N/cm and a recovery rate when extended to 100% of at least about 90% are effectively employed. Further, base materials having a 50% extensibility (a stress exerted when it is extended to 50%) of about 1 to 4.9 N/cm and a recovery rate when extended to 50% of at least about 90% may also effectively be employed. Such materials include, for example, fabrics having fine continuous filaments of polyurethane elastic fibers randomly laminated, the cross points of which are bonded.

As the adhesive of the adhesive layer 2 formed on the surface of the base material 1, adhesives of acryl, rubber, silicone, vinyl, etc. may be appropriately employed. Particularly, when acryl adhesives are employed, stimulation against the skin will be reduced, which is preferable. The adhesive is provided entirely or partly on one surface, such as the top surface, of the base material 1 so that it can be stuck and fixed to the wound area as described below.

On the adhesive layer 2, a pad 3 is placed firmly. The pad 3 has a size such that when the injection needle, etc. is inserted into an arterial blood vessel 15 through the skin surface of the patient (FIG. 5), the pad 3 will cover both a puncture 16 of the arterial blood vessel and a puncture 17 of the skin surface at the same time for applying pressure to both punctures.

The distance between the punctures 16 and 17 differs depending on the area of the body to be punctured, the age of the patient, such as child or adult, and the patient's sex. However, the size of the pad 3 is usually about 1 to 4 cm in the long side. The pad 3 is formed in an appropriate shape such as rectangular, square, circle, oval, elliptical and polygon. In the case of oval, elliptical and rectangular shapes, the ones having a ratio of short side to long side up to about 1:4 are preferred. In the case of square and circle shapes, a ratio of 1:1 is preferred. Thus, the ratio is usually within the range of from about 1:1 to about 1:4.

When the pad 3 is formed in a shape having corners, for example, rectangular, square and polygon, if the corner areas are formed in an arc shape, unwanted stimulation against the skin surface is reduced. When the pad 3 is formed in an elliptical shape with the long side being about 20 to 40 mm and the short side being about 10 to 20 mm, both the puncture of the artery and the puncture at the skin surface are simultaneously pressed in most cases, which is preferable.

Further, the pad 3 preferably has a hardness capable of securely pressing the puncture and has, for example, not only a slight elasticity but also an appropriate compression strength so that the pad is not readily deformed when pressed. The pad 3 has sufficient thickness to enable the pad to press the puncture when applied against the puncture area, and the thickness is at least 3 mm, and usually about 3 to 20 mm, although the thickness differs depending on the applicable area. If the pad is too thin, pressing cannot be effectively conducted.

The sticking materials having a thin pad are suitable to hemostasis for dorsalis pedis arteries, etc., and the ones having a thick pad are suitable to hemostasis for femoral arteries, etc. When the pad becomes thick, the pressure will be strong, but the pad may rarely happen to be crushed horizontally or collapsed, which is not preferable. In many cases, the preferred pad thickness is about 5 to 13 mm.

The pad 3 is formed in a multi-layer structure. Preferably, a cushion layer 4, a lower layer 5, an upper layer 6 and a surface layer 7 are sequentially formed on the adhesive layer 2. The cushion layer 4 has an elasticity at a level of a slight hardness so as to obtain the desired pressing effect and has sufficient recovery action to prevent occurrence of the so-called settling phenomenon. The lower layer 5 is a layer capable of transmitting the pressing action and capable of absorbing blood, and is softer and more fluffy than the cushion layer 4. The upper layer 6 is softer and more fluffy than the lower layer 5, so that it will make soft contact with the puncture and the blood will be absorbed rapidly. The surface layer 7 is formed thin so that napping of the upper layer 6 will be prevented and peeling off of the coagulated blood will be facilitated.

The pad 3 is preferably made of, for example, the following materials. The cushion layer 4 is formed of plastic foam, such as polyethylene foam having a large content of isolated cells, or compressed cotton, such as compressed cotton of polyester unwoven cloth. For the lower layer 5, compressed cotton, such as compressed cotton of cellulose unwoven cloth, or a laminated rayon cotton, is employed. For the upper layer 6, unwoven cloth, such as rayon unwoven cloth, is employed. For the surface layer 7, perforated polyethylene film, nylon net, rayon net, a thin cellulose unwoven cloth, etc. are employed.

An example effective to hemostasis of an artery is one wherein the cushion layer 4 is made of polyethylene foam having a large content of isolated cells and occupies about 50 to 70% of the entire thickness, the lower layer 5 is made of cellulose unwoven compressed cotton and occupies about 20 to 30% of the thickness, the upper layer 6 is made of a rayon unwoven cloth and occupies about 20% of the thickness, and the surface layer 7 is a perforated polyethlene film.

The lower layer 5 and the upper layer 6 may be formed as a single layer by using a material having the properties required for both layers to form a three-layer structure as a whole. Further, the lower layer 5, the upper layer 6 and the surface layer 7 may be formed as a single layer to form a two-layer structure as a whole.

The pad 3 is usually located at the central portion of the base material 1 so that the sticking material can be stuck over the puncture with the adhesive layer 2 provided on the base material 1. However, depending on the site of application, the pad 3 may be localized at one side of the base material 1 for easy handling. Although the base material 1 is sometimes formed in the shape of a square, circle, oval, etc., preferred is often a long strip shape.

When the pad 3 is placed on the long strip-shaped base material 1, it is advisable to place the pad such that the long side of the pad extends in the short side direction (transverse direction) of the base material. Further, the pad covers in its long side both the puncture of the arterial blood vessel and the puncture of the skin surface whereby the pressing action can readily be conducted. Thus, after the pressing, the adhesive layer is stuck to the skin surface of the patient, whereby satisfactory hemostasis can simply and securely be conducted. In the embodiment as shown in FIG. 1 and FIG. 2, an elliptical pad 3 is placed such that the long side of the pad extends at a right angle to the longitudinal direction of the long strip-shaped base material 1, such being preferred for pressing. However, the pad 3 may be placed obliquely at an angle other than a right angle.

Figure 5:
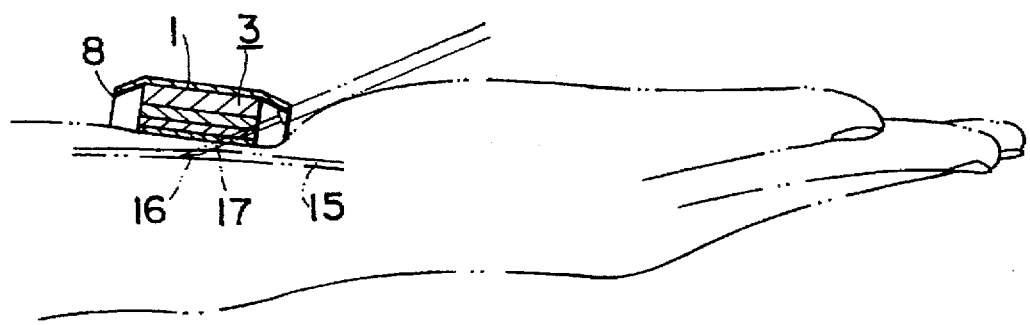
FIG. 5 is an explanatory view showing the sticking material for hemostasis of FIG. 1 when used for hemostasis of an artery.

The pad 3 is preferably placed with a space 9 of a length shorter than the thickness of the pad, i.e., a distance of usually about 3 to 10 mm, preferably about 6 mm, from both side edges 8,8 of the base material 1. By such a structure, when the base material 1 is stuck to the patient's skin, the portion of the space 9 of the base material is folded to cover both sides of the pad and the pressing action is exerted obliquely inwardly and downwardly. Thus, the pressing action is concentrated toward the pad without scattering, whereby the thick pad is more securely prevented from moving horizontally or collapsing (FIG. 5). Further, since the space 9 is narrow as mentioned above, when an injection needle is removed while pressing with the pad during use of the sticking material, the injection needle, etc., will not be in contact with the base material 1 having the adhesive layer, etc., and no interruption of the procedure will be caused, as described below.

Figure 3:
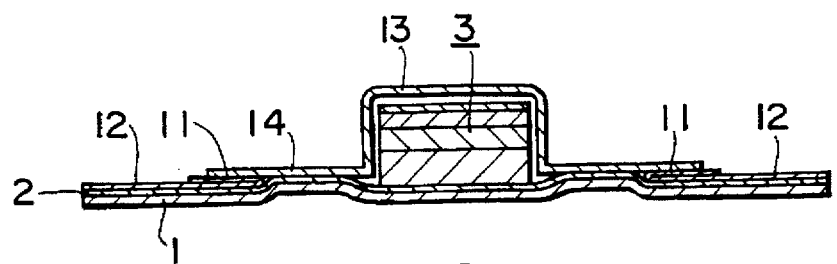
FIG. 3 is a cross-sectional view showing the sticking material for hemostasis of FIG. 1 in the packaged condition.

It is advisable to cover the surface of the adhesive layer 2 and pad 3 of the base material 1 of the sticking material 10 for hemostasis formed as above with a release paper. It is preferred to package the sticking material 10 with a bag for hygiene and easy handling. The package shown in FIG. 3 is obtained by covering the adhesive layer on both sides of the pad 3 with a release paper 12 having a folding strip 11, and further putting thereon a cap 14 made of a plastic having an enclosing portion 13 for the pad 3, whereby the pad can be hygienically maintained without distortion. Such a material may be sealed in a packaging bag obtained by weakly and removably adhering a pair of packaging sheers with a sealing agent, etc., or, as the case requires, may be sealed in such a packaging bag without using the cap 14 (not shown in the drawing).

Figure 4:
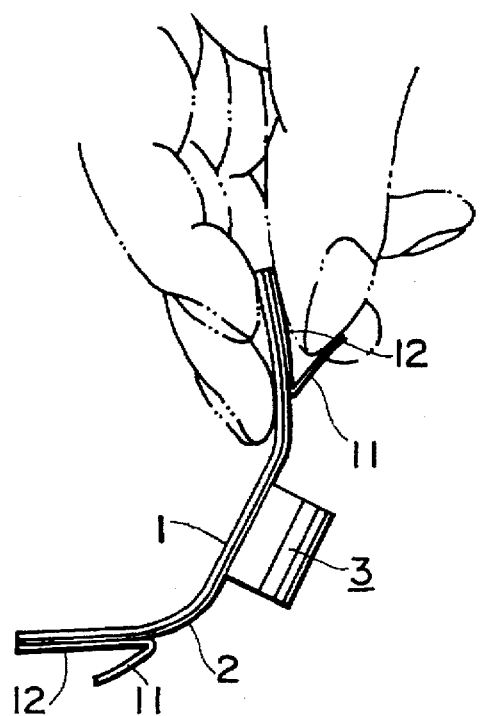
FIG. 4 is an explanatory view showing the sticking material for hemostasis of FIG. 1 in use.

When the sticking material 10 is used, referring to the embodiment shown in FIGS. 1 to 3, the cap 14 is removed and the base material 1 is grasped while inserting the thumb between the release paper 12 and the folding strip 11 (FIG. 4).

For example, when a needle of about 22 to 23 gauge (outer diameter 0.72–0.66 mm) is used for blood extraction or a catheter of about 20 gauge (outer diameter 0.91 mm) is used at the radial artery of the wrist, before the needle or the catheter is removed, the pad 3 is attached to the puncture area such that the long side thereof extends in the direction that the needle is inserted at the puncture area, i.e., the direction that the ductus arteriosus 15 lies, and the needle or the catheter is removed while pressing the pad. Further, one release paper 12 is peeled off while pressing the pad so that the exposed adhesive layer 2 is stuck to the skin such that it will cross the direction that the ductus arteriosus lies while pulling and stretching the base material slightly, and then the other release paper 12 is pulled at its folding strip 11 and released, and the exposed adhesive layer 2 is stuck onto the skin while pulling and stretching the base material 1 slightly to fix the sticking material 10 to the skin.

By such a procedure, the pad 3 is located over the puncture 16 of the ductus arteriosus under the skin and also covers the puncture 17 of the skin surface. Then the pad 3 is pressed downward by the shrinking action of the stretched base material 1. Further, the pad 3 presses the skin downward strongly although the press is soft due to the multi-layer structure including the cushion layer 4. Thus, the area of the puncture 16 of the ductus arteriosus 15 is pressed concentratedly and strongly and closed, whereby the hemostasis can be securely conducted. By the pressing action, bleeding from the puncture 17 of the skin surface will result after removal of the needle. However, the blood will be immediately and readily absorbed by the surface layer 7 of the pad 3, and if the bleeding amount is much more, the blood will penetrate into the upper layer 6 to be absorbed and held therein whereby no blood will leak out.

After the sticking material 10 is applied to the puncture area for a certain period of time, the hemostasis is completed. The sticking material 10 can be removed from the skin surface about 5–30 minutes, generally about 10–20 minutes, after being stuck to skin surface, whereby no contamination of the clothes, etc. by bleeding will result.

When the sticking material 10 is adhered to the wrist as described above, if the base material 1 does not encircle the entire periphery of the wrist, blood circulation of other blood vessels will not be disturbed and the hemostasis of the important area can adequately be conducted, which is advantageous.

Figure 6:
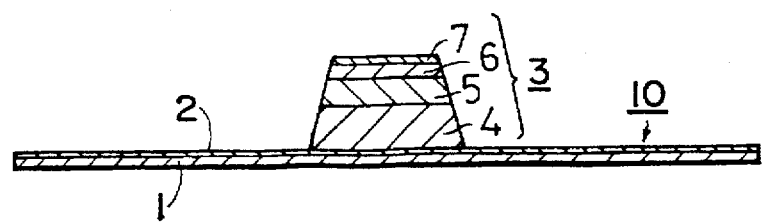
FIG. 6 is a cross-sectional view showing another embodiment of the sticking material for hemostasis according to the present invention.

The sticking material 10 for hemostasis as shown in FIG. 6 is produced by making the shape of the pad 3 in a trapezoid shape, wherein the side just above the adhesive layer 2 of the base material 1 is made larger than the other side. This sticking material 10 makes it possible to press the pad 3 against the puncture under more stable condition, whereby the pad will hardly be collapsed and the hemostasis will be effectively conducted.

Figure 7:
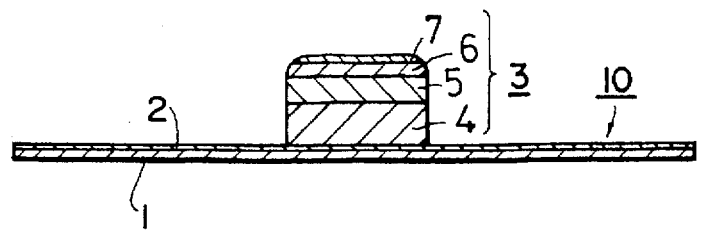
FIG. 7 is a cross-sectional view showing a further embodiment of the sticking material for hemostasis according to the present invention.

In the sticking material 10 for hemostasis as shown in FIG. 7, the corners of the surface layer 7 and the upper layer 6 of the pad 3 are cut off or rounded in an arc shape so that the sticking material 10 can adapt to the shape of the skin surface, whereby the contact with the skin will be more mild.

Figure 8:
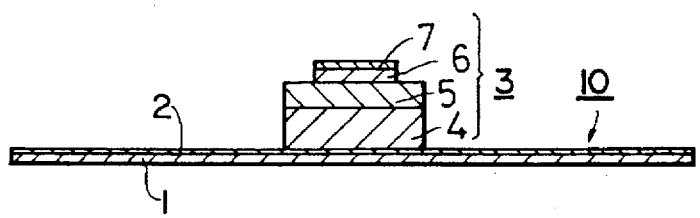
FIG. 8 is a cross-sectional view showing still another embodiment of the sticking material for hemostasis according to the present invention.

In the sticking material 10 for hemostasis as shown in FIG. 8, the surface layer 7 which makes contact with the skin and the upper layer 6 of the pad 3 are designed to be slightly smaller than the lower layer 5 and cushion layer 4, whereby the stability when the pad 3 is fixed is further increased and the pressing action will be made concentratedly.

Figure 9:
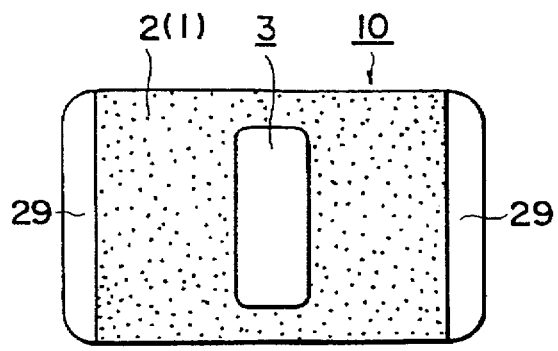
FIG. 9 is a plan view showing another modified embodiment of the sticking material for hemostasis according to the present invention.

In the sticking material 10 for hemostasis as shown in FIG. 9, a non-adhesive portion 29 is provided at opposite ends of the base material 1 by omitting the adhesive layer 2 at both edge areas of the base material 1 or by sticking non-adhesive sheets at the edge areas. When the sticking material 10 is to be peeled off the skin after the hemostasis is completed, the non-adhesive portion 29 is readily grasped and thus the sticking material 10 can readily be peeled off. The non-adhesive portion 29 can be disposed only at one edge area of the base material 1.

Figure 10:
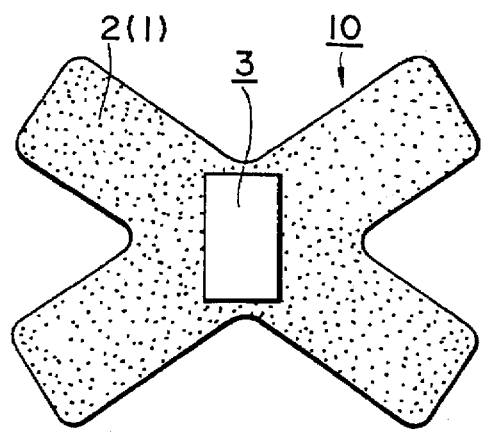
FIG. 10 is a plan view showing a further modified embodiment of the sticking material for hemostasis according to the present invention.

In the sticking material 10 for hemostasis as shown in FIG. 10, the base material is formed in an X-shape, and a pad 3 is placed at the central portion thereof. This configuration is sometimes useful to fix and press the pad to the puncture area more securely.

The sticking materials 10 for hemostasis as shown in FIGS. 6 to 10 can be stuck to the wound area of a patient in the same manner as described above with reference to FIGS. 1–5.

Figure 12:
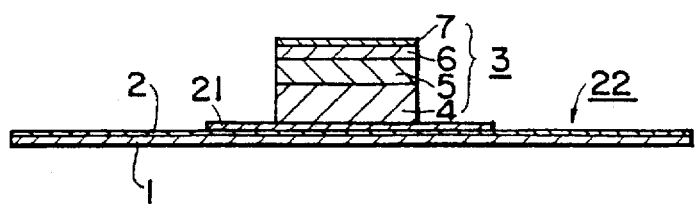
FIG. 12 is a cross-sectional view of the sticking material shown in FIG. 11.
Figure 11:
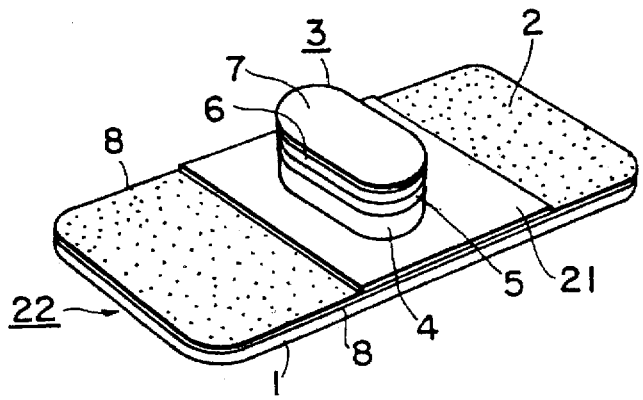
FIG. 11 is a perspective view showing another embodiment of the sticking material for hemostasis according to the present invention.

FIGS. 11 and 12 show another embodiment of a sticking material 22 for hemostasis which has a pressure or pressing plate 21 made of a thin and tough strip-shaped material such as plastic, metal, plywood or the like, interposed between the adhesive layer 2 and the pad 3. The pressing plate 21 is formed larger in size than the pad 3. It is advisable to form the pressing plate 21 to have a length of about 3 to 10 cm in the longitudinal direction of the base material 1, and the length is usually about 4 to 7 cm. In the embodiment shown in the drawings, the width of the pressing plate 21 is made the same size as the width of the base material 1, and the elliptical-shaped pad 3 is fixed on the pressing plate such that the long side of the pad 3 extends at the right angle to the longitudinal direction of the long strip-shaped base material 1. Such a structure is a preferred embodiment for use with an arterial blood vessel. However, the pad 3 may be placed to extend obliquely as mentioned above. Also, the pad 3 may be placed such that it is shifted toward one side of the pressing plate 21 rather than being centrally located.

The sticking material 22 for hemostasis can be used for hemostasis of an artery in the same manner as above. The shrinking action of the stretched base material, which shrinks during the use, is concentrated toward the pad 3 by the large pressing plate 21, and serves to strongly press it downward. By this action, the area of the puncture 16 of the ductus arteriosus 15 will be pressed concentratedly and closed, whereby hemostasis can be made more securely.

Figure 13:
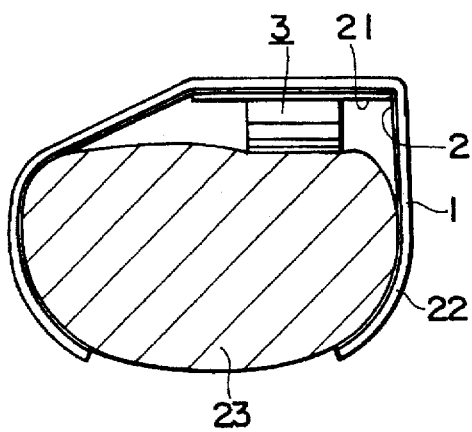
FIG. 13 is an explanatory view showing the sticking material for hemostasis of FIG. 11 in use.

As shown in FIG. 13, the area on the skin surface to which the base material 1 is not stuck becomes wide by means of the pressing plate 21, so that it will rarely happen that the base material 1 will disturb the blood circulation of the ulnar artery and the vein other than the punctured radial artery of the arm portion 23. Thus, the hemostasis can be conducted by adequately pressing the puncture area without causing cyanosis, etc., and the stimulation by the adhesive against the skin will be reduced, which is preferable. Further, if the pressing plate 21 is flexed or bent when the sticking material 22 for hemostasis is applied, the pressing action by means of the pad 3 may sometimes be further strengthened by the recovery action of the pressing plate 21.

Figure 14:
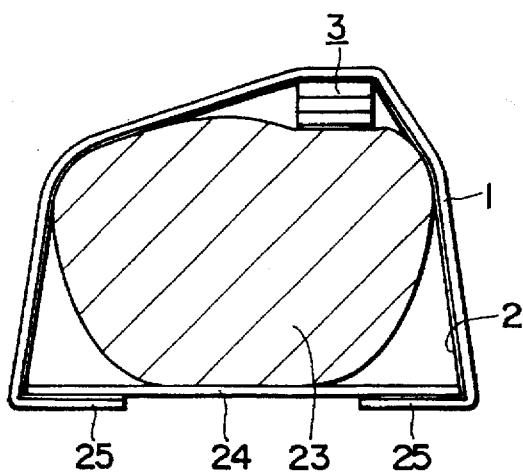
FIG. 14 is a an explanatory view showing the sticking material for hemostasis according to the present invention in another use.

In the sticking material for hemostasis as shown in FIG. 14, the pad 3 is placed on the adhesive layer 2 of the base material 1 as in the embodiment shown in FIG. 1, and the pad 3 is placed to cover the puncture of the blood vessel. Then, a pressing plate 24 is located on the skin surface at the side of the skin surface opposite to that having the pad 3, with the arterial blood vessel interposed, and both edge portions 25,25 of the base material are stuck to the pressing plate 24 to fix the sticking material to the wound area. This structure also provides secure hemostasis.

Figure 15:
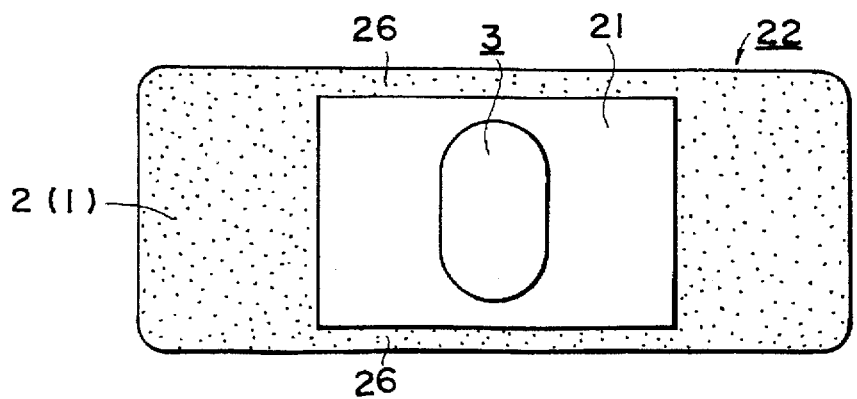
FIG. 15 is a plan view showing another embodiment of the sticking material for hemostasis according to the present invention.

In the sticking material 22 for hemostasis as shown in FIG. 15, the width of the pressing plate 21 is made narrower than the width of the base material 1. When the sticking material 22 is stuck to the wound area, as explained with respect to FIG. 5, the spacer areas 26,26 at both sides of the base material 1 are folded to cover both sides of the pressing plate 21 and will exert pressing action downwardly and obliquely inwardly. Thus, the pressing action is concentrated from the pressing plate toward the pad without scattering, thereby further preventing the thick pad from shifting horizontally or being collapsed.

Figure 16:
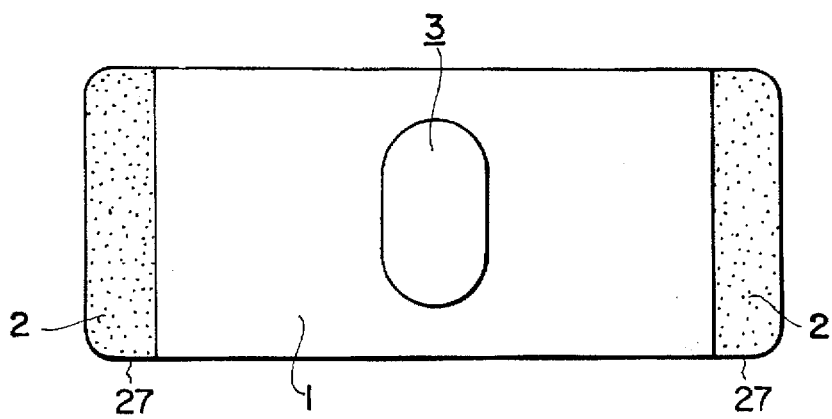
FIG. 16 is a plan view showing a further embodiment of the sticking material for hemostasis according to the present invention.

In the sticking material for hemostasis as shown in FIG. 16, an adhesive layer 2 is disposed only at both edge portions 27,27 of the base material 1. This sticking material is used in the same manner as the embodiment shown in FIG. 14, and, since the area of the adhesive layer 2 is small, the pressing action and the stimulation action against the skin other than the puncture area is small, which is preferable in many cases.

Figure 17:
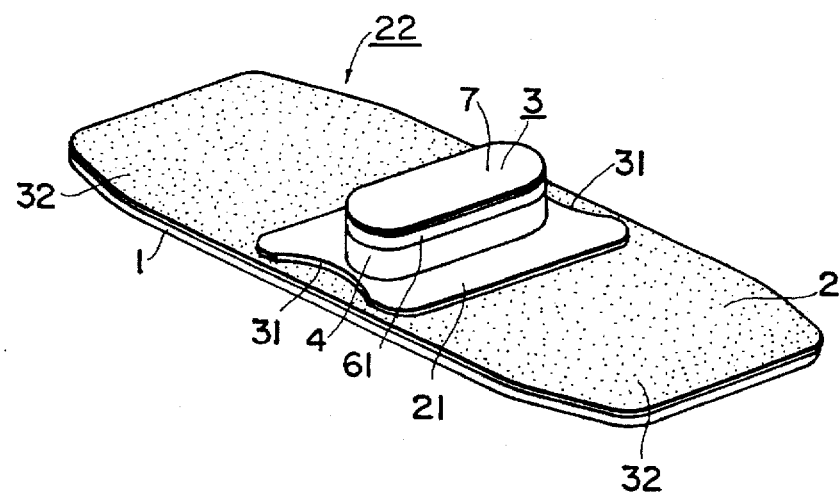
FIG. 17 is a perspective view showing another embodiment of the sticking material for hemostasis according to the present invention.

In the sticking material 22 for hemostasis as shown in FIG. 17, a concave portion 31 is provided at the central portion of opposite side edges of the pressing plate 21 along the longitudinal direction of the base material 1, and each corner of the concave portions 31 is formed in an arc shape. When this sticking material 22 is used, if the concave portions 31,31 of the pressing plate are picked up from the base material side, the longitudinal center line of the pad 3 will be naturally known, and thus the pad 3 can be brought in contact with both punctures securely and readily. The concave portions 31 serve to further prevent the pressing plate 21 from being in contact with the inserted needle, etc. Since both edge portions 32 in the longitudinal direction of the base material 1 gradually become narrower in width, the base material 1 can readily be stretched by pulling the base material 1 at the portions 32.

Figure 18:
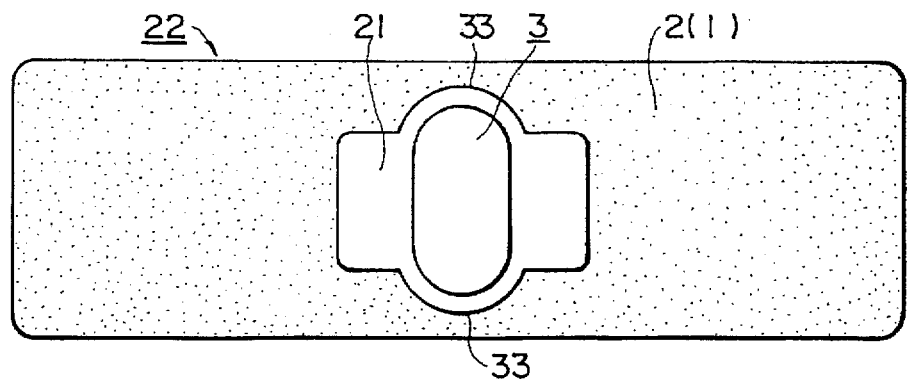
FIG. 18 is a plan view showing still another embodiment of the sticking material for hemostasis according to the present invention.
Figure 19:
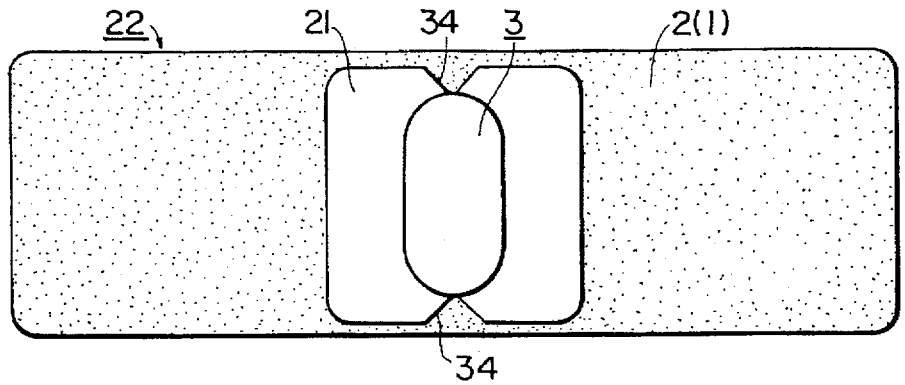
FIG. 19 is a plan view showing a further embodiment of the sticking material for hemostasis according to the present invention.

In the sticking material 22 for hemostasis as shown in FIG. 18, convex portions 33 are provided on the pressing plate 21 instead of the concave portions 31 of the pressing plate shown in FIG. 17. In the sticking material 22 for hemostasis as shown in FIG. 19, V-shaped concave portions 34 are provided. The convex portions 33 and the V-shaped concave portions 34 provided on the pressing plate 21 make it easy to find the position of the pad 3 when it is stuck to the wound area, as in the case of the concave portions 31.

Figure 20:
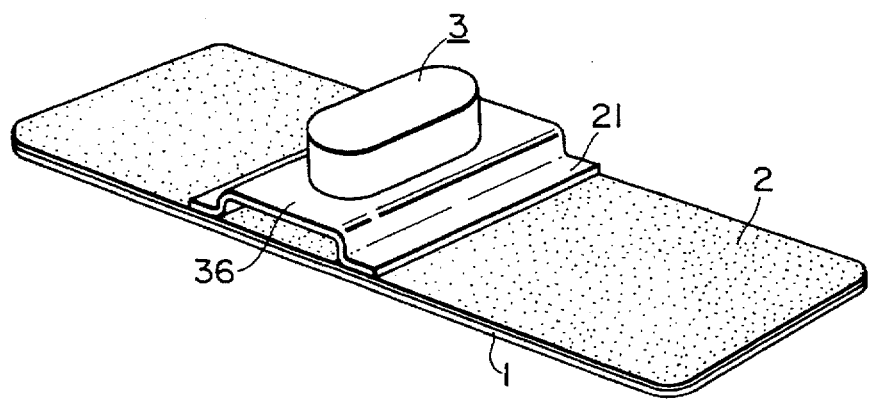
FIG. 20 is a perspective view showing another embodiment of the sticking material for hemostasis according to the present invention.
Figure 21:
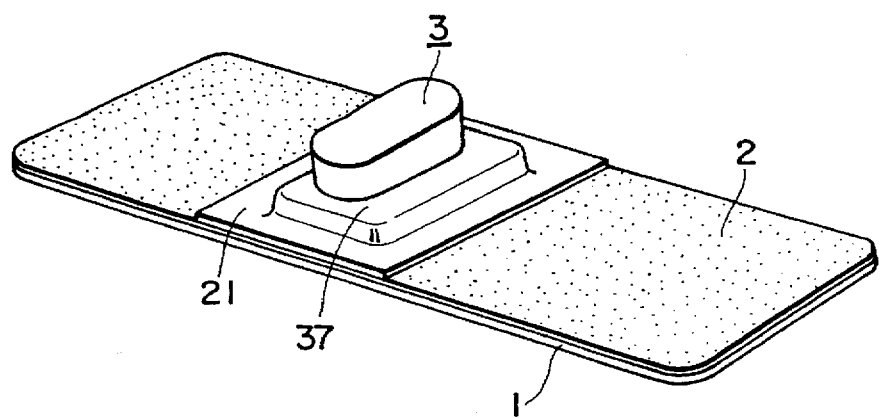
FIG. 21 is a perspective view showing still another embodiment of the sticking mateiral for hemostasis according to the present invention.

The above-mentioned pressing plates all have a plate-like shape. However, the pressing plate may have a raised or protruded portion at one part thereof with the pad placed on the protruded portion, as shown in the embodiments of FIGS. 20 and 21. In the sticking material as shown in FIG. 20, a bent protruded portion 36 is formed at the central portion of the pressing plate 21. In the sticking material as shown in FIG. 21, a raised or protruded portion 37 is formed by press forming or the like at the central portion of the pressing plate 21. Such a protruded portion can also be formed by stacking a small strip on a large strip. In such a sticking material having a protruded portion disposed on a pressing plate, the pressing action can further be strengthened due to the height of the protruded portion, whereby it is further easily applied to the hemostasis for a femoral artery, etc. for which hemostasis is hardly applicable.

Figure 22:
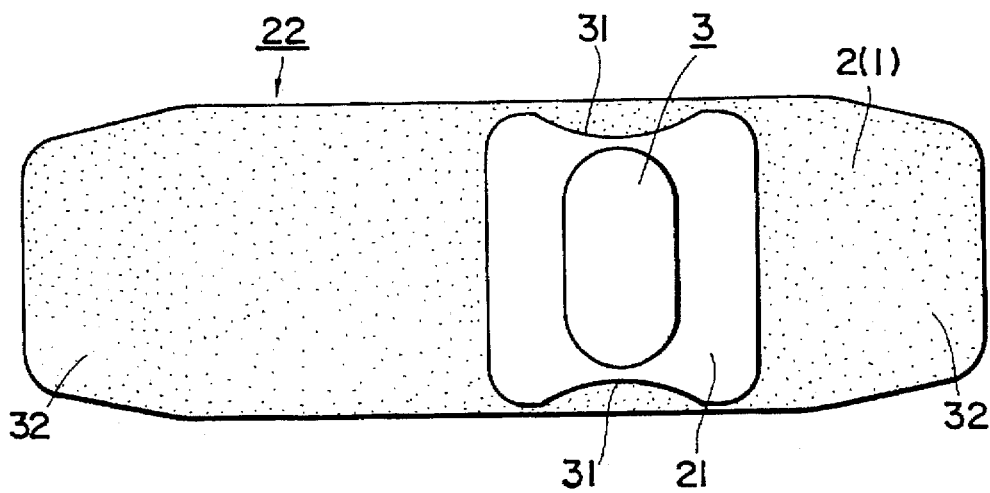
FIG. 22 as a plan view showing another embodiment of the sticking material for hemostasis according to the present invention.

In the above mentioned embodiments, the pad alone or the combination of the pad and the pressing plate are located at the central portion in the longitudinal direction of the base material. However, as in the sticking material 22 for hemostasis shown in FIG. 22, the pads, etc. may be placed in such a manner that they are shifted toward one end of the base material 1 in the longitudinal direction. Such a sticking material is sometimes conveniently applicable to situations wherein the blood vessel, such as a radial artery, ulnar artery or dorsalis pedis artery, is locally placed on the arm, etc.

Figure 23:
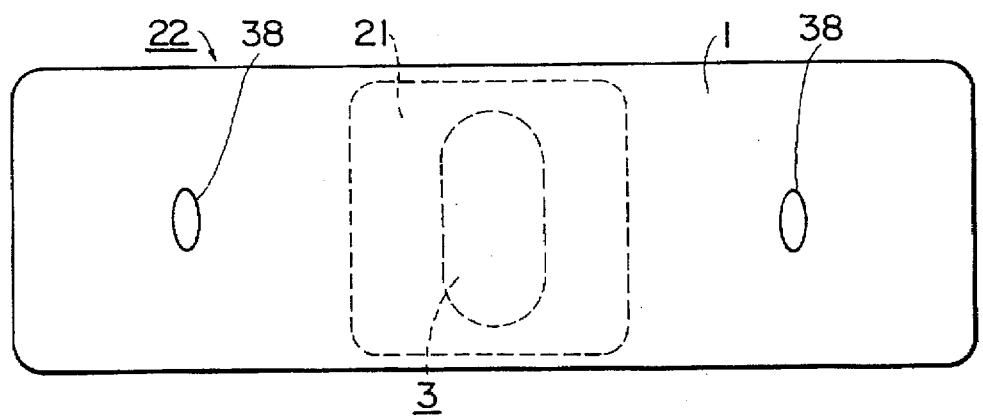
FIG. 23 is a plan view showing still another embodiment of the sticking material for hemostasis according to the present invention.
Figure 24:
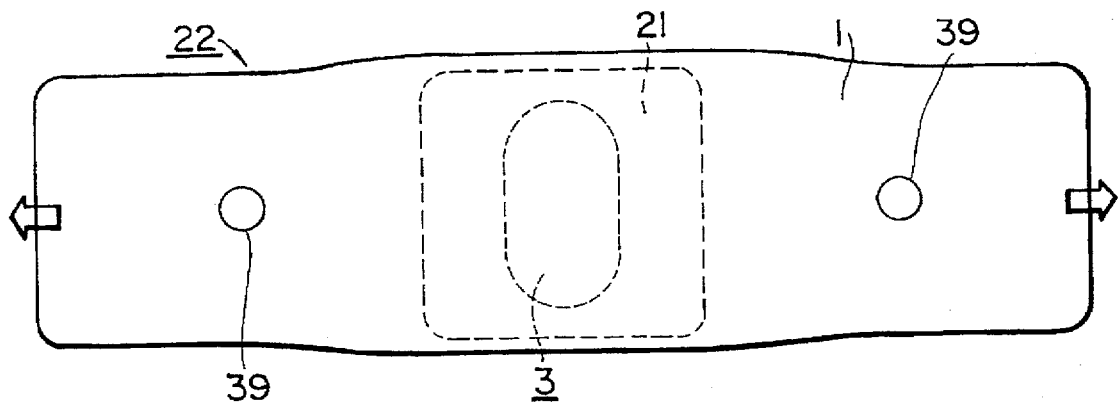
FIG. 24 is a plan view showing the sticking material for hemostasis according to the present invention when the substrate thereof is extended.

Reference will next be made to FIGS. 23 and 24, which show use of indicators on the base material 1 to monitor the degree of stretching of the base material. In FIG. 23, indicators in the form of distorted circular FIGS. 38 are indicated at the surface of a stretchable base material 1 opposite to the adhesive layer. When the sticking material 22 is used, by lengthwise pulling the base material 1, the base material elongates and the distorted circular FIG. 38 (FIG. 23) become circle FIG. 39 (FIG. 24). When the base material 1 is stuck to the skin surface under this condition, the desired pressing action can readily be obtained by the shrinking base material. As such an index showing the degree of extension of the base material, various indicators of different shapes, such as equilateral triangle and the like, can be used in addition to the circle shape.

The bleeding stoppage to the ductus arteriosus is carried out as mentioned above. The blood extraction, drip of water, blood transfusion, artificial dialysis, etc. are carried out by puncturing the injector needle, catheter, medical tube, etc. into the venous blood through the surface of the skin.

After pulling the injector needle out, the venipunctured portion also starts bleeding, and it is therefore necessary to stop the bleeding by pressing an absorbent cotton or gauze by finger strongly and pressing the absorbent cotton by adhesive tapes and/or flexible bandage, etc. However, it takes about ten minutes or more to stop bleeding by pressing the punctured portion by finger or other means fixedly, which is not only troublesome but also unreliable, because omission of a steady pressure leads to hypodermic bleeding, and the blood which is blurred over from the aperture of the punctured portion is unsightly and likely to spoil the clothing of the patient. Moreover, some patients are not in a position to press the punctured portion by fingers or other means.

Furthermore, in case of a thin injector needle, the aperture of the punctured portion to the blood vessel is also small, and the bleeding stoppage is relatively easy to the venous blood. On the other hand, in case of a thick injector needle, the aperture of the punctured portion becomes large, which results in bleeding of a large quantity of blood, and the bleeding stoppage is more difficult than in case of the thin injector needle. The present invention can effectivley stop bleeding of arteries. For example, when a relatively thick injector needle of 16 to 18 gauge (outer diameter 1.67~1.26 mm) is used for blood extraction and blood transfusion, sure bleed stoppage is possible. Of course, the bleeding stoppage is carried out more easily in case of using a thin injector needle.

EXAMPLE 1

A sticking material product (product 1) according to the present invention was prepared and the results of measurement of the pressing force of this product are shown below.
Product 1
Base material: The base material was obtained by randomly laminating fine continuous filaments comprising 100% of polyurethane elastic fibers, and bonding the crossing points of the respective filaments. The properties are shown below:

| Stress at 100% extension | Longitudinal direction 4.8N/cm |
| --- | --- |
|  | Latitudinal direction 3.7N/cm |
| Recovery at 100% extension | Longitudinal direction 90% |
|  | Latitudinal direction 90% |
| Breaking strength | Longitudinal direction 17.2N/cm |
|  | Latitudinal direction 13.2N/cm |

Figure 25:
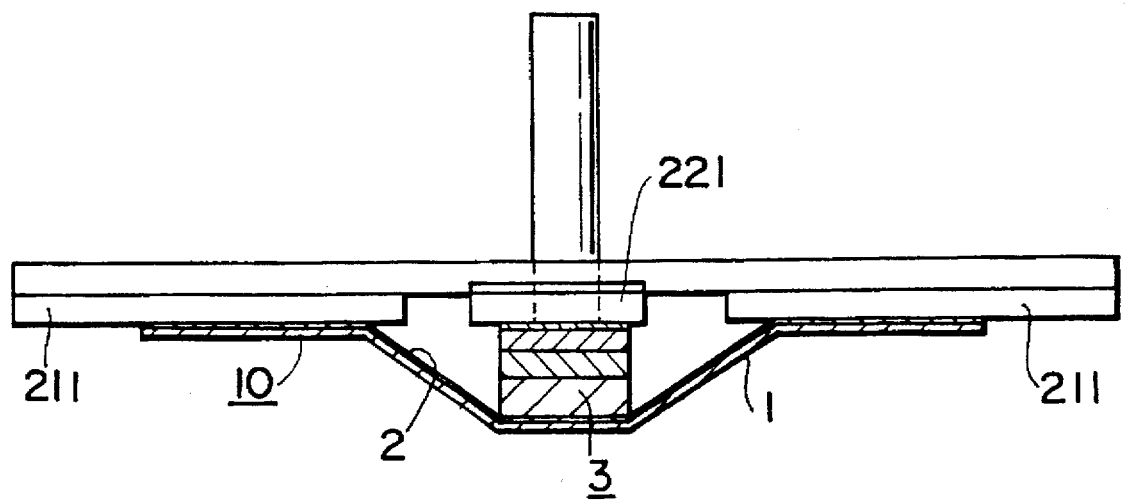
FIG. 25 is an explanatory view showing an apparatus for measuring the pressing force of the sticking material for hemostasis according to the present invention.

The above material was cut in a rectangular shape of 45×100 mm having arc-shaped corners, the longitudinal direction of which was the long side.
Adhesive layer: Acryl type adhesive was used.
Pad: The surface layer was cellulose unwoven cloth having a thickness of 0.05 mm.
The upper layer was rayon unwoven cloth having a thickness of 2.3 mm.
The lower layer was a compressed cotton of cellulose unwoven cloth having a thickness of 2.7 mm.
The cushion layer was a sheet of a foam of polyethylene isolated cells having a thickness of 5 mm.
Shape: An elliptical shape having a long side of 27 mm, a short side of 15 mm and a thickness of 10 mm.
Measurement of the Pressing Force
The pressing force of product 1 was measured by an apparatus as shown in FIG. 25. The adhesive layer of product 1 was stuck to a measurement platform 211 made of Bakelite, and the pad 3 was pressed with a probe 221 having a diameter of 20 mm so that the surface of the probe could be adjusted to the surface of the platform 211 with a rheometer. The pressing force after 1 minute was measured. The measurement was conducted with respect to 10 products of the same construction.
Results
The pressing force was 360±12 gf/cm$^3$.
Comment
Sufficient pressing force was obtained by product 1 and this product was confirmed to be useful as a hemostatic material for arteries.

EXAMPLE 2

Product 2 was prepared and the results of measurement of the pressing force, pressure sense, numbness and change of palm color when this product was used are shown below.
Product 2
Base material: The base material was obtained by randomly laminating fine continuous filaments comprising 100% of polyurethane elastic fibers, and bonding the crossing points of the respective filaments. The properties are shown below:

| Stress at 50% extension | Longitudinal direction 2.6N/cm |
| --- | --- |
|  | Latitudinal direction 1.96N/cm |
| Recovery at 50% extension | Longitudinal direction 90% |
|  | Latitudinal direction 90% |
| Breaking strength | Longitudinal direction 12.7N/cm |
|  | Latitudinal direction 9.9N/cm |

The above material was cut in a rectangular shape of 45×100 mm having arc-shaped corners, the latitudinal direction of which was the long side.
Adhesive layer: Acryl type adhesive was coated to 38±2 g/m$^2$.
Pressing plate: A polyvinylchlorine plate having a thickness of 1.1 mm was cut in a size of 45×50 mm and stuck to the adhesive layer at the central portion thereof, while adjusting the edges.

Pad: The surface layer was cellulose unwoven cloth having a thickness of 0.05 mm.

The upper layer was rayon unwoven cloth having a thickness of 2 mm.

The lower layer was a compressed cotton of cellulose unwoven cloth having a thickness of 2 mm.

The cushion layer was a sheet of a foam of polyethylene isolated cells having a thickness of 5 mm.

Shape: An elliptical shape having a long side of 27 mm, a short side of 15 mm and a thickness of 9 mm.

This pad was fixed at the central portion of the pressing plate such that the long side of the pad extended in the transverse direction of the base material.

Position, Time and Method for Sticking

The pad was put on the radial artery of a testee's left wrist while extending or stretching the sticking material to 140 mm, and then the sticking material was stuck in the same manner as shown in FIG. 13 for 1 minute.

EXAMPLE 3

Product 3

Product 3 was prepared using the same base material, adhesive and pad as product 2 provided that the pad was placed at the central portion of the base material.

Pressing Plate: A polyvinylchloride plate with a thickness of 1.1 mm was cut in a size of 45×70 mm.

Position, Time and Method for Sticking

The pad was put on the radial artery of a testee's left wrist and the pressing plate was located at the side opposite to the pad. Then, while extending the base material to 140 mm, it was stuck to the pressing plate in the same manner as shown in FIG. 14 for 1 minute.

Contrast Compared with Examples 2 and 3

There is not a pressing plate in the Contrast Example in other respects, the Constrast Example is the same as Example 2.

Position, Time and Method for Sticking

The pad was put on the radial artery of a testee's left wrist while extending or stretching the sticking material to 140 mm, and then the sticking material was stuck for 1 minute.

Items of Measurement and Observation

Measurement of the force of pressure under the pad portion: At the carpal portion of the radial artery, a pouch of a catheter for measurement of cerebrospiral pressure, connected to a piezoelectric transducer, was noninvasively fixed. The sticking material was stuck such that the pad portion was located on the pouch. Then, the pressing force at the pad portion was measured.

The pressure sense, numbness, change of palm color as a side effect: 1 minute after application of the sticking material, the pressing, feeling and the numbness were verbally asked to the testee, and the discoloration of the testee's palm was observed with the naked eye.

Testee: six persons

Method of Evaluation

The force of pressure at the pressed area was read from a recording sheet and then converted to numerical values (mmHg) and the average (mean) value thereof was determined.

The pressure sense, numbness and change of palm color were evaluated by four steps of "none, weak, medium and strong". These steps were assigned numerical values 0, 1, 2 and 3, respectively, and the average (mean) value thereof was determined.

| Results | | | |
| --- | --- | --- | --- |
| | Example 2 | Example 3 | Control |
| Force of pressure (average, mmHg) | 246 | 143 | 85 |
| Pressure sense (average) | 3.0 | 2.2 | 1.5 |
| Numbness (average) | 1.2 | 0.8 | 1.0 |
| Change of palm color (average) | 0.7 | 0.5 | 1.2 |

Comment

In each of Examples 2 and 3, a larger pressing force was obtained as compared with the control, and thus the pressing feeling is slightly strong. However, the change of palm color was less than in the Contrast Example and thus improved. Accordingly, Examples 2 and 3 hardly influence human bodies, and are effective and useful for hemostasis of arteries.

EXAMPLE 4

Product 4 was prepared and the results of measurement of the pressing force, side effect (pressing, feeling, numbness, discoloration of palm), the time required for vanishing the pressure marks, and stimulus of the skin surface by changing the extension length of the base material are shown below:

Product 4

The structure of product 4 is as shown in FIG. 17.

Base material: The base material was obtained by randomly laminating fine continuous filaments comprising 100% of polyurethane elastic fibers, and bonding the crossing points of the respective filaments. The properties are shown as below:

| | |
| --- | --- |
| Weight | 100 g/m² |
| Stress at 50% extension | Longitudinal direction 4.9N/20 mm |
| | Latitudinal direction 3.6N/20 mm |
| Recovery at 100% extension | Longitudinal direction 87% |
| | Latitudinal direction 87% |
| Strength of extension | Longitudinal direction 15.7N/20 mm |
| | Latitudinal direction 11.8N/20 mm |
| Extension | Longitudinal direction 370% |
| | Latitudinal direction 380% |

The above base material was cut in a rectangular shape of 40×126 mm having gradually narrowed edges, the latitudinal direction being the long side (FIG. 17).

Adhesive layer: Acryl type adhesive was coated to 40 g/m².

The properties of the adhesive coated on the above base material were as follows:

Adhesive strength: 1.96N/15 mm

Tack (rolling ball method): No. 31

Pressing plate: A polyprophylene plate of 1 mm thickness was cut in a square of 36×36 mm with arc-shaped corners and having convex portions on opposite sides (FIG. 17).

This pressing plate was adhered to the adhesive layer at the central portion of the sticking material such that the convex portions along extended the longitudinal direction of the base material.

Pad: The surface layer was cellulose unwoven cloth having a thickness of 0.05 mm.

The upper layer was rayon unwoven cloth having a thickness of 3 mm.

The cushion layer was a sheet of a foam of polyethylene isolated cell having a thickness of 6 mm and having the following properties:

| | |
|---|---|
| density at glande | 0.067 g/cm³ |
| commmpressed hardness | 0.64 Kg/cm² |

Shape: An elliptical shape having a long side of 27 mm, a short side of 15 mm and a thickness of 9 mm.

This pad was fixed at the central portion of the pressing plate such that the long side of the pad extended in the transverse direction of the base material (FIG. 17).

Position, Time and Method for Sticking

The pads were put on the radial arteries of testee's left and right wrists, and the sticking material was stuck for 1 minute under the following four conditions:

(1) while not extending the sticking material (2) while extending the sticking material by 1 cm on each opposite side (total 2 cm)

(3) while extending the sticking material by 2 cm on each opposite side (total 4 cm)

(4) while extending the sticking material by 3 cm on each opposite side (total 6 cm)

The pressing force of this sticking material and the condition of the skin after applying the sticking material for one hour (1 hr) were measured.

Testing Method

Measurement of force of pressure under the pad portion: Measurement was carried out in the same manner as in Examples 2 and 3. The pressing force of the pressure body at the time of adhering and one hour later were measured from a recording sheet and indicated as numerical values (mmHg), whose mean value and±standard deviation were determined.

Side effect (pressure sense, change of palm color and numbness): One-hour after adhesion, the pressure sense and numbness of the testees were checked, and the change of palm color was observed by eye.

The evaluations (ratings) are as follows: five stages, none, weak, medium, rather strong and strong; each step being assigned numerical values 0, 1, 2, 3 and 4, respectively, and whose average value (mean) and±standard deviation was determined.

Adhesion and peeling condition: The condition of adhesion, and the residue of the adhesive, were evaluated in peeling the adhesive bandage one hour later.

Time required for disappearance of the pad mark: After peeling the sticking material, pressure marks caused by the pads were observed by eye and the time for disappearance of the pad marks was measured.

Dermal irritation index: The reaction of the skin with the adhesive attached was evaluated according to the following standard four-hour later and 24-hour later after peeling, respectively, and the dermal irritation index was noted.

| | | |
|---|---|---|
| − 0 | | no reaction |
| ± 0.5 | | weak erythema |
| + 1.0 | | erythema |
| ++ 2.0 | | erythema + edema |
| +++ 3.0 | | erythema + edema + palule or serous palule or visicle |
| ++++ 4.0 | | bulla |
| Dermal irriation index | | total/testees × 100 |
| Sample number of each extension: 12 | | |

Results (1) Adhesion and peeling condition: No peeling (removal) was found, and favorable adhesion condition was maintained. No residue of the adhesive was found at the skin surface after peeling.

(2) The pressure sense, side effect (pressure sense, change of palm color, numbness), time required for vanishing the pressure marks, and skin stimulus indication number were as follows:

| | 0 cm | 1 cm | 2 cm | 3 cm |
|---|---|---|---|---|
| The force of pressure (mmHg) | | | | |
| Initial | 11 ± 6 | 79 ± 18 | 112 ± 19 | 141 ± 26 |
| 1-hour after application | 9 ± 6 | 68 ± 16 | 98 ± 17 | 121 ± 17 |
| Side effect (5 classes) | | | | |
| Pressure sense | 0.0 ± 0.0 | 0.4 ± 0.6 | 0.9 ± 0.6 | 1.4 ± 0.6 |
| Change of palm color | 0.0 ± 0.0 | 0.2 ± 0.4 | 0.3 ± 0.4 | 0.5 ± 0.5 |
| Numbness | 0.0 ± 0.0 | 0.2 ± 0.4 | 0.2 ± 0.4 | 0.5 ± 0.6 |
| Disapperance of the pad mark (hr) | | | | |
| disapperance time | 0.8 ± 0.4 | 2.7 ± 0.5 | 3.2 ± 0.6 | 3.6 ± 0.6 |
| Dermal irritation index (D.I.I.) | | | | |
| 4 hr | 0.0 | 0.0 | 0.0 | 4.2 |
| 24 hr | 0.0 | 0.0 | 0.0 | 0.0 |

Comment

As a whole, the adhering condition was favorable, since no peeling was found, and no residue of the adhesive was found after peeling.

When the base material was extended by 2 cm and 3 cm, respectively, the pressing force over the usual systolic blood pressure was attained. One hour after sticking, the pressing force decreased by 10–20 mmHg, but it was favorable in view of the release of the pressure after hemostasis.

The side effect after one-hour usage of product 4 was very small, i.e., there was no problem in use.

When the base material was extended by 3 cm, the base material surrounded the periphery of the wrist, but no side effect was found. This is because the pressing plate allowed the ulnar artery blood to flow surely.

Thus, when used by extending about 2 cm, product 4 can give proper pressure action, and various side effects are very small even after long use. Therefore, it may be used as the sticking material for hemostasis of arteries.

According to the present invention, as mentioned above, it is possible to securely conduct the hemostasis of the puncture of an artery, and effective hemostasis can be made to arteries located close to bones, such as the ulnar artery and the dorsalis pedis artery, in addition to the radial artery. Further, the present invention is applicable to the femoral artery. Effective hemostasis can be made to veins also in the same manner as applied to the artery. Further, the procedure in use is easy and the structure of the sticking material is simple, whereby the production can be made economically.

We claim:

1. An adhesive material for hemostasis, comprising: a flexible strip-shaped base member having a high recovery property, a main surface, and side edges extending in a first longitudinal direction; an adhesive layer disposed on the main surface of the base member; and a pad having opposite ends and being disposed on the adhesive layer and extending in a second longitudinal direction substantially transverse to the first longitudinal direction such that a space is defined between each end of the pad and a respective one of the side edges of the base member, the pad comprising a layer composed of a material for preventing the deposition of coagulated blood when the pad is applied against a puncture area, the pad being of a size sufficient to directly contact and exert pressure at the puncture area including punctures of both a blood vessel and a skin surface, the pad having a slight elasticity and a hardness capable of securely exerting pressure on the punctures by a shrinking action of the base member when the base member is adhered to the skin surface while being stretched to secure the pad over the punctures.

2. An adhesive material as claimed in claim 1; wherein the pad has an elliptical shape having a length of from 20 to 40 mm, a width of from 10 to 20 mm and a thickness of from 8 to 12 mm.

3. An adhesive material as claimed in claim 1; wherein the length of the space defined between each end of the pad and a respective one of the side edges of the base member is less than the thickness of the pad.

4. An adhesive material as claimed in claim 1; wherein the pad has a ratio of length to width of from 1:1 to 4:1.

5. An adhesive material as claimed in claim 1; wherein the pad comprises at least one layer composed of an absorbent material for absorbing blood from the puncture area.

6. An adhesive material as claimed in claim 1; wherein the pad has an elliptical shape and a thickness of from 3 to 20 mm.

7. An adhesive material as claimed in 6; wherein the length of the space defined between each end of the pad and a respective one of the side edges of the base member is less than the thickness of the pad.

8. An adhesive material for hemostasis, comprising: a strip-shaped base member having a main surface; an adhesive layer disposed on the main surface of the base member; a pressure plate disposed on the adhesive layer and having a width equal to or less than the width of the base member; and a pad disposed centrally on the pressure plate and having a thickness of from 3 to 20 mm, the pad being of a size smaller than the size of the pressure plate and sufficient to exert pressure at a puncture area including punctures of both a blood vessel and a skin surface, the pad having a slight elasticity and a hardness capable of securely exerting pressure to the punctures when the pad is applied against the puncture area; wherein the base member has side edges extending in a first longitudinal direction, and the pad extends in a second longitudinal direction substantially transverse to said first longitudinal direction such that a space is defined between the pressure plate and each of the side edges of the base member.

9. An adhesive material as claimed in claim 8; wherein the length of the space defined between the pressure plate and each of the side edges of the base member is less than the thickness of the pad.

10. An adhesive material as claimed in claim 8; wherein the pressure plate comprises side edges extending in the first longitudinal direction, each of the side edges having a convex portion.

11. An adhesive material as claimed in claim 8; wherein the pressure plate comprises a raised portion, the pad being disposed on said raised portion.

12. An adhesive material as claimed in claim 8; wherein the pressure plate comprises side edges extending in the first longitudinal direction, each of said side edges having a concave portion.

13. An adhesive material as claimed in claim 12; wherein the concave portion is V-shaped.

14. An adhesive material for hemostasis, comprising: a flexible base member; an adhesive layer disposed on the base member; a pressure plate disposed on the adhesive layer and having a width less than the width of the base member; and a pad disposed on the pressure plate, the pad being of a size sufficient to exert pressure at a puncture area including punctures of both a blood vessel and a skin surface, the pad having a slight elasticity and a hardness capable of securely exerting pressure to the punctures when the pad is applied against the puncture area.

15. An adhesive material as claimed in claim 14; wherein the base member is strip-shaped.

16. An adhesive material as claimed in claim 14; wherein the pad has a size smaller than the size of the pressure plate.

17. An adhesive material as claimed in claim 14; wherein the pad is a multi-layer structure comprising a first layer disposed on the adhesive layer for exerting a pressure in a thickness direction of the base member, a second layer disposed on the first layer for exerting a pressure thereon and absorbing blood from the puncture area, a third layer disposed on the second layer for rapidly absorbing blood from the puncture area, and a fourth layer disposed on the third layer for preventing deposition of coagulated blood.

18. An adhesive material for hemostasis, comprising: a flexible strip-shaped base member having a high recovery property, a main surface, and side edges extending in a first longitudinal direction; an adhesive layer disposed on the main surface of the base member; and a pad having opposite ends and being disposed on the adhesive layer and extending in a second longitudinal direction substantially transverse to the said first longitudinal direction such that a space is defined between each end of the pad and a respective one of the side edges of the base member, the pad being of a size sufficient to directly contact and exert pressure at a puncture area including punctures of both a blood vessel and a skin surface, the pad having a slight elasticity and a hardness capable of securely exerting pressure on the punctures by a shrinking action of the base member when the base member is adhered to the skin surface while being stretched to secure the pad over the punctures; wherein the pad is a multi-layer structure comprising a cushion layer disposed on the adhesive layer for exerting a pressure in a thickness direction of the base member, a lower layer disposed on the cushion layer for exerting a pressure thereon and composed of an absorbent material for absorbing blood from the puncture area, an upper layer disposed on the lower layer and composed of an absorbent material for rapidly absorbing blood from the puncture area, and a surface layer disposed on the upper layer and composed of a material for preventing deposition of coagulated blood.

19. An adhesive material for hemostasis, comprising: a strip-shaped base member having a main surface; an adhesive layer disposed on the main surface of the base member; a pressure plate having a width less than the width of the base member; and a pad disposed centrally on the pressure plate, the pad being of a size smaller than the size of the pressure plate and sufficient to exert pressure at a puncture area including punctures of both a blood vessel and a skin surface, the pad having a slight elasticity and a hardness capable of securely exerting pressure to the punctures when the pad is applied against the puncture area.

20. An adhesive material for hemostasis, comprising: a strip-shaped base member having a main surface; an adhesive layer disposed on the main surface of the base member; a pressure plate disposed on the adhesive layer and having a width equal to or less than the width of the base member; and a pad disposed centrally on the pressure plate, the pad being of a size smaller than the size of the pressure plate and sufficient to exert pressure at a puncture area including punctures of both a blood vessel and a skin surface, the pad having a slight elasticity and a hardness capable of securely exerting pressure to the punctures when the pad is applied against the puncture area; wherein the pad is a multi-layer structure comprising a first layer disposed on the adhesive layer for exerting a pressure in a thickness direction of the base member, a second layer disposed on the first layer for exerting a pressure thereon and absorbing blood from the puncture area, a third layer disposed on the second layer for rapidly absorbing blood from the puncture area, and a fourth layer disposed on the third layer for preventing deposition of coagulated blood.

21. A method for hemostasis, comprising the steps of:

placing over both a puncture of a blood vessel and a puncture on a skin surface a pad comprising a material having a slight elasticity and a hardness capable of securely exerting pressure on the punctures;

disposing on the pad a pressure plate having a size larger than the pad and comprising a material having a higher strength than the material of the pad;

disposing over the pressure plate and the pad a base member having an adhesive layer and composed of a flexible material having a high recovery property, the base member having a width greater than the pressure plate; and adhering the base member to the skin surface while stretching the base member to secure the pressure plate and the pad over the punctures such that the pad is pressed toward the punctures through the pressure plate by a shrinking action of the base member.

22. A method for hemostasis as claimed in claim 21; wherein the pad has a thickness of from 3 to 20 mm.

23. A method for hemostasis, comprising the steps of:

placing over both a puncture of a blood vessel and a puncture on a skin surface a pad comprising a material having a slight elasticity and a hardness capable of securely exerting pressure on the punctures;

placing over a skin surface opposite the skin surface containing said puncture a pressure plate having a size larger than the pad and comprising a material having a higher strength than the material of the pad;

disposing over the pad a strip-shaped base member having an adhesive layer and composed of a flexible material having a high recovery property, the base member having a width greater than the pressure plate; and adhering opposite ends of the base member to the pressure plate while stretching the base member to secure the pressure plate and the pad over respective skin surfaces such that the pad is pressed toward the punctures through cooperation of the pressure plate by a shrinking action of the base member.

24. A method for hemostasis as claimed in claim 23; wherein the pad has a thickness of from 3 to 20 mm.

* * * * *